United States Patent
Stein

[19]

[11] Patent Number: 5,932,789

[45] Date of Patent: Aug. 3, 1999

[54] BOLT THREAD INSPECTION AND THREAD POLISHING DEVICE

[76] Inventor: Ronald B. Stein, P.O. Box 178, Prospect Park, Pa. 19076

[21] Appl. No.: 08/520,206

[22] Filed: Aug. 21, 1995

[51] Int. Cl.$^6$ .............................. G01N 3/56; G01M 19/00
[52] U.S. Cl. ................................... 73/7; 451/294
[58] Field of Search ................... 73/7, 865.8; 451/294

[56] References Cited

U.S. PATENT DOCUMENTS

| | | | |
|---|---|---|---|
| 4,014,062 | 3/1977 | Scott et al. | 15/104.04 |
| 4,016,938 | 4/1977 | Rice | 73/761 X |
| 4,077,808 | 3/1978 | Church et al. | 501/80 |
| 4,403,363 | 9/1983 | Hess | 15/104.04 |
| 4,644,394 | 2/1987 | Reeves | 348/131 |
| 4,988,325 | 1/1991 | Alderson et al. | 446/397 |
| 5,043,377 | 8/1991 | Nogi et al. | 524/437 |
| 5,157,802 | 10/1992 | Guidry et al. | 15/88 |
| 5,309,490 | 5/1994 | Bayersten | 376/310 |
| 5,366,524 | 11/1994 | Holcombe, Jr. et al. | 51/293 |
| 5,568,263 | 10/1996 | Hanna | 356/385 |

Primary Examiner—Thomas P. Noland

[57] ABSTRACT

A device for the timely and accurate inspection of and polishing of large threaded bolts. The device is easily reconfigured for effective use on a large number of different sized bolt threads by replacing the polishing stones, depending on the dimensions of the particular bolt thread. After a metal layout dye is placed on the bolt threads the rotating polishing stones reveal the upset and damaged threads that must be repaired before replacing the corresponding nut.

5 Claims, 6 Drawing Sheets

BOLT THREAD INSPECTION AND THREAD POLISHING DEVICE

BACKGROUND OF THE INVENTION

1. Field of the Invention

The present invention pertains to the maintenance and repair of power generating machines; preferably, but not exclusively, turbine engines. More specifically, the present invention relates to the preparation of the large threaded bolts that must be carefully inspected as to avoid gauld threads in the reassembling of these large industrial machines. During their lifetime the bolt threads are dented and damaged. Without isolating and repairing upset bolt threads, before replacing their corresponding nuts, the nuts can become stuck and/or the costly bolt destroyed.

2. Related Art

Until now the inspection of such bolts has been a slow and time consuming process requiring simple visual examination. When a particular thread is judged unacceptable by the examiner, a metal file is used to work the suspected damage out of the bolt thread. One aspect of particular difficulty with this method is that many times the damaged thread is not obvious to the unaided eye. Mistakes or errors in visual inspections cause considerable loss of productivity, as nuts must then be repeatedly removed due to unforeseen thread damage, as well as unnecessary efforts expended filing workable threads.

In order to provide background information of related art so that the invention may be appreciated and understood in its own context reference may be made to the following U.S. patents:

U.S. Pat. Nos. 5,309,490 (Bayerstern): 5,157,802 (Guidry et al.): 4,403,363 (Hess): and 4,014,062 (Scott et al.)
Note: all which pertain to using brushes for threaded bolt cleaning.

No device is known to aid exclusively in the detection of upset and damaged threads of large industrial bolts as this invention advances the art.

SUMMARY OF THE INVENTION

The principal object of the present invention is to provide an effective device for the timely and accurate inspection of threads on large industrial bolts. The subject device in accordance with the present invention comprises at least one pair of diametrically opposed legs, a means for clamping the legs and polishing stones attached to a distal end of the legs. The subject invention can easily be reconfigured for effective use on a large number of different sized bolts. This is accomplished by readily replacing the polishing stones to accommodate the diameter size and the number of threads of the particular bolt. The present invention may also comprise a lightweight portable turning device which can be powered from any number of drill drivers (manual or mechanical). So as to make the device interchangeable with different sized bolts, there preferably is a spring-loaded clamp positioned on the adjacent arms of the turning device. On each arm of the turning device there are holes through which the polishing stones are attached, preferably by way of cotter pins. The present invention further utilizes a separate mixture of epoxy-resin & abrasive powder to provide heat-molded polishing stones that vary in dimension as threaded bolts increase in increments both through standard and metric measure. Thus, depending on the diameter of the bolt and the thread pitch, a particular pair of polishing stones would be attached to the turning device. Then, the bolt would be painted with standard metal layout dye (such as Dykem). The turning device would clamp into place and the revolution of the threaded polishing stone will bring forth to a shine any upset or damaged areas in the bolt threads. These damaged areas can then be readily and positively identified and the thread repaired by conventional means.

DESCRIPTION OF THE PREFERRED EMBODIMENT

Figure 1A:
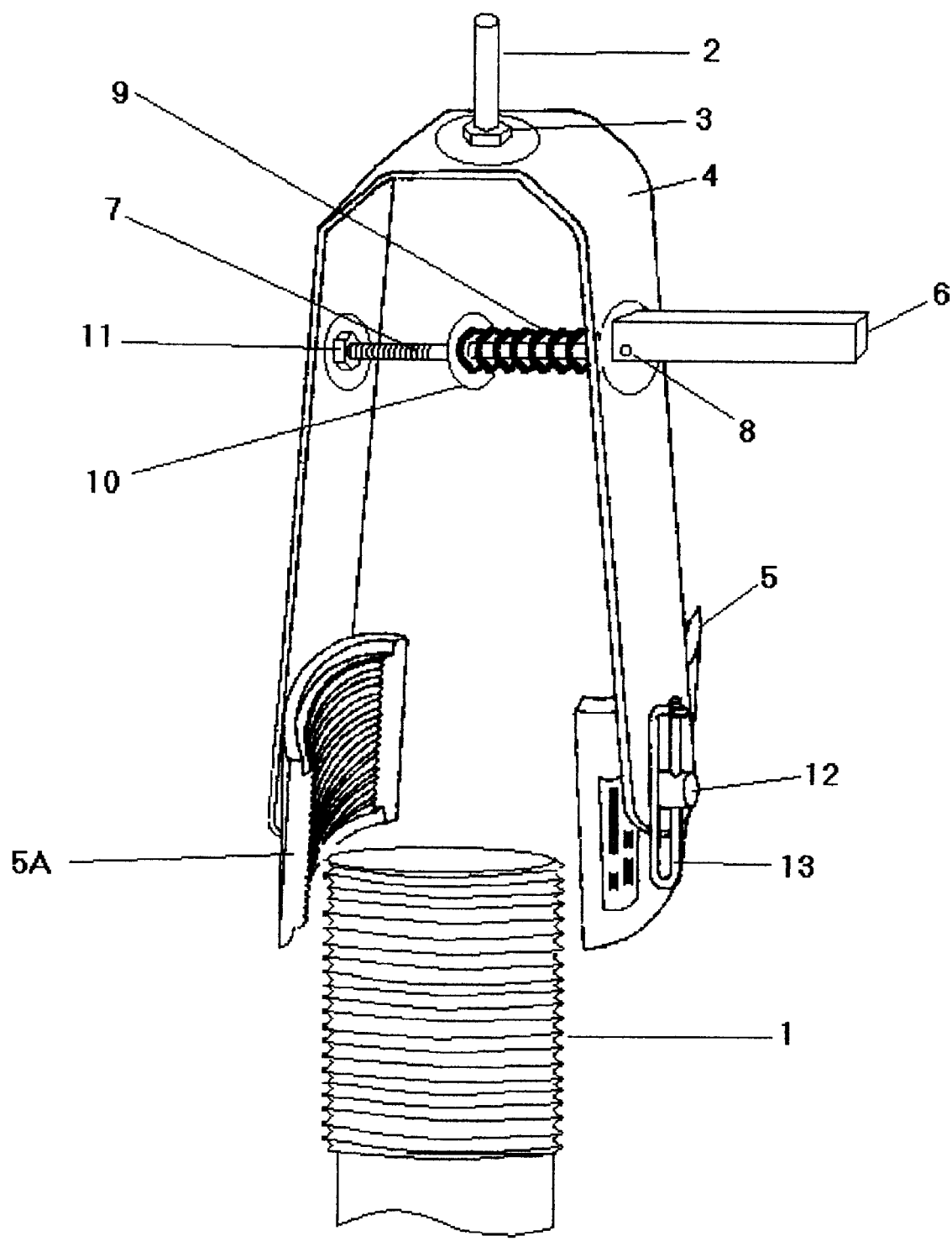
FIGS. 1A,1B are horizontal perspective views of the turning device of the present invention with attached polishing stones.

With reference now to the FIGURES wherein reference characters designate similar or like parts throughout the several views.

Figure 1B:
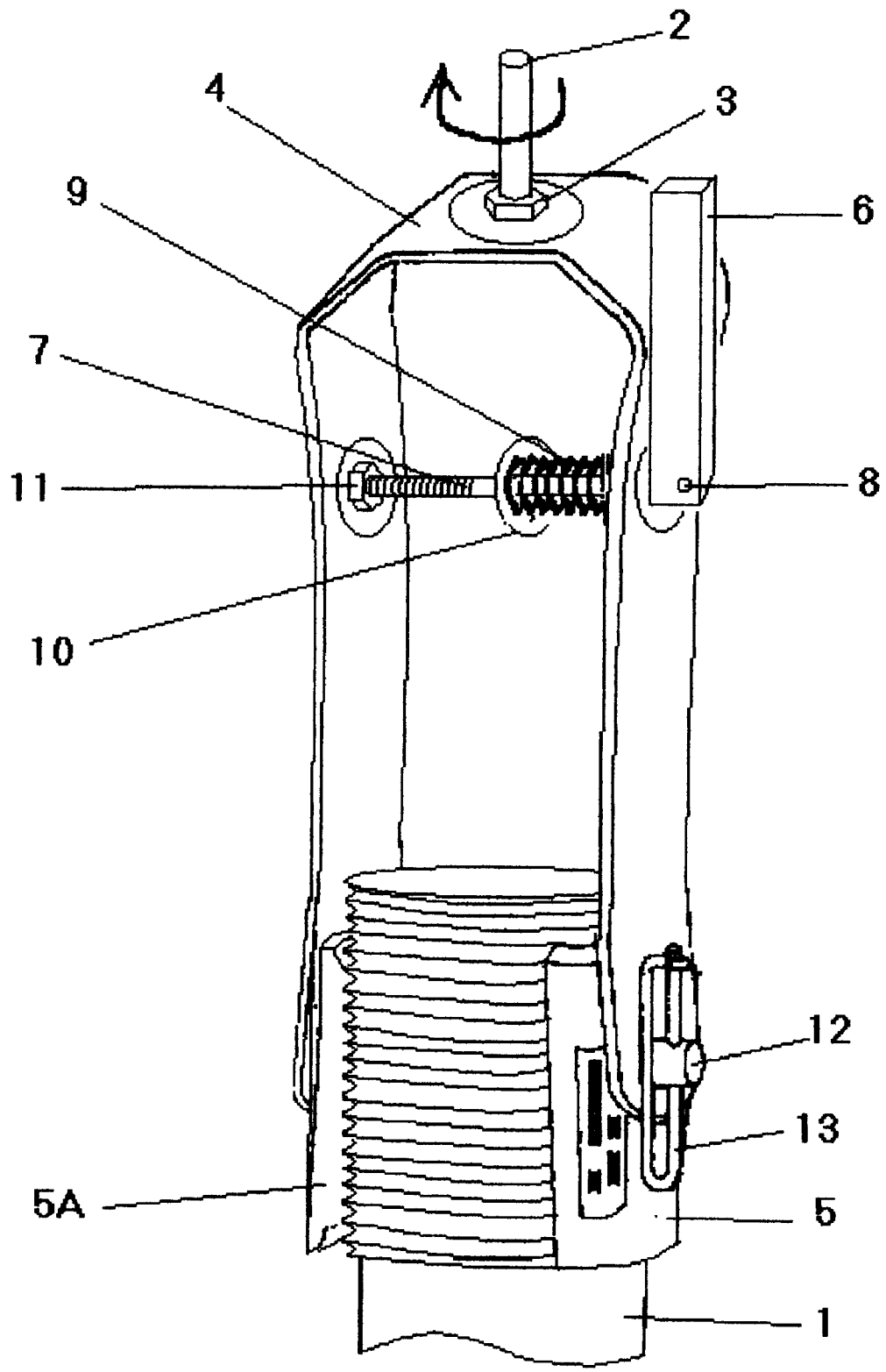

FIGS. 1A & 1B are perspective views of the large bolt thread inspection and thread polishing device 10; FIG. 1A prior to attachment to bolt threads 8a, FIG. 1B attached to bolt thread 8a.

The shank part 1, to be coupled with a rotating drill driver, is secured to the body of the tool 11 so as to remain fixed to the body 11 during rotation. The shank 1 is secured to the body of the tool 11 by the head bolt nuts 2,3.

The opposing arms of the body 11 bring the polishing stones 9,9a to bear on the bolt threads 8a by way of the flipping action of the spring-loaded clamp 5. The clamp handle 5a is connected to the clamp rod 5e by a rotatable pin 5b. The spring 5d is fixed in place by the spring nut 5c. The clamp rod is anchored to the body of the tool 11 by the clamp rod nut 5f.

The turning device comprises a lightweight portable U-shaped metal frame. The base of the U-shaped metal frame is defined as the proximate end, while the open portion of the U-shaped frame is defined as the distal end. A polishing stone is mounted on the distal end of each leg of the U-shaped frame, and a shank is preferably located at the proximate end.

The shank allows the turning device to be rotated by a variety of drill drivers (manually or mechanically). So as to make the device easily interchangeable with bolts of varying dimensions, a spring-loaded clamp is used to adjust the legs of the turning device.

In the preferred embodiment, holes are drilled proximate the distal end of each arm of the turning device. A mounting bolt, attached to the polishing stones, passes through its respective hole and is secured with a cotter pin.

The polishing stones are prepared using a mold. The polishing stone contains an epoxy abrasive mixture with external threads using internal thread parameters.

Near the ends of the arms of the body of the tool 11 on the width wise center lines are holes to connect the polishing stones 9,9a via the connecting shafts 7,7a. Cotter pins 6,6a through the connecting shafts 7,7a secure the polishing stones 9,9a to the body of the tool 11. The threaded stones 9,9a are fixed to the connecting shafts 7,7a during the molding process of the polishing stones 9,9a. In use, the large bolt thread inspection and thread polishing device 10 can be adjusted manually by closing the spring-loaded clamp 5 after a particular pair of polishing stones 9,9a, depending on the diameter of the bolt and the thread pitch, have been attached.

The bolt threads 8a are preferably painted with a standard metal layout dye (such as Dykem) prior to the attachment and subsequent rotating of the polishing stones 9,9a. Once properly secured the device 10 may be rotated about the bolt threads using either a mechanical or manual drill. The device 10 is readily removed from the bolt threads 8a by releasing the spring-loaded clamp 5. The revolution of the threaded polishing stone 9,9a will bring forth to a shine any upset or damaged areas in the bolt threads 8a. These damaged areas can then be readily and positively identified and the thread repaired by conventional means.

Figure 2A:
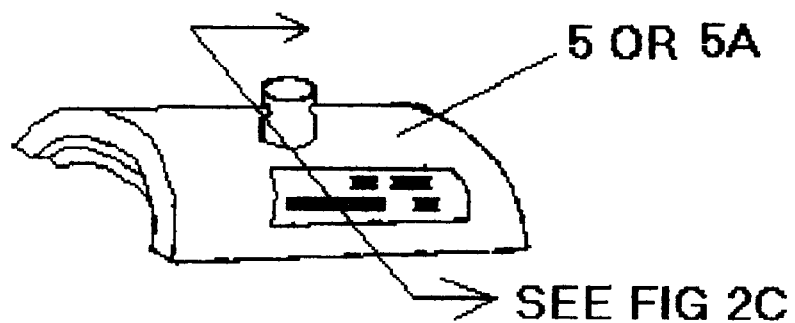
FIG. 2A is a top side perspective view of the polishing stone, 2B is a bottom side perspective, 2C is a cross section.
Figure 2B:
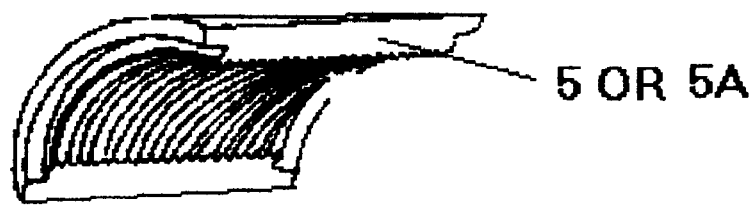
Figure 2C:
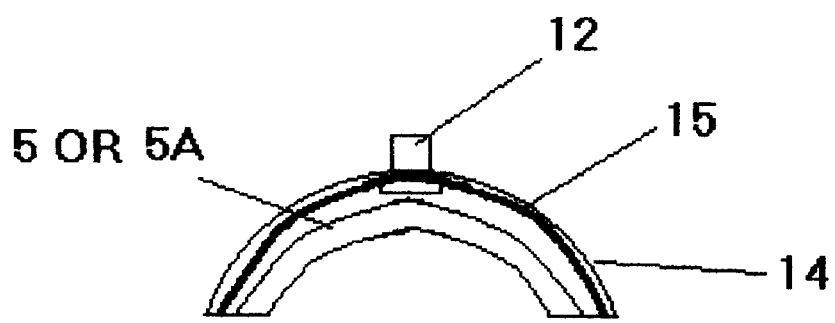

FIG. 2a is top perspective of the polishing stone and FIG. 2b is a bottom side perspective of the same. FIG. 2c gives reference to the axial centerline cross section of the preferred embodiment of the polishing stone. The body of the stone 15 is composed of an epoxy abrasive mixture covered by a cloth 12. The cloth 12 is impregnated with an epoxy mixture and an optional pigment. In order to connect the polishing stone to the turning device a connecting bolt 7 is set within the epoxy mold and secured by a bent bracing strap 14.

Figure 3:
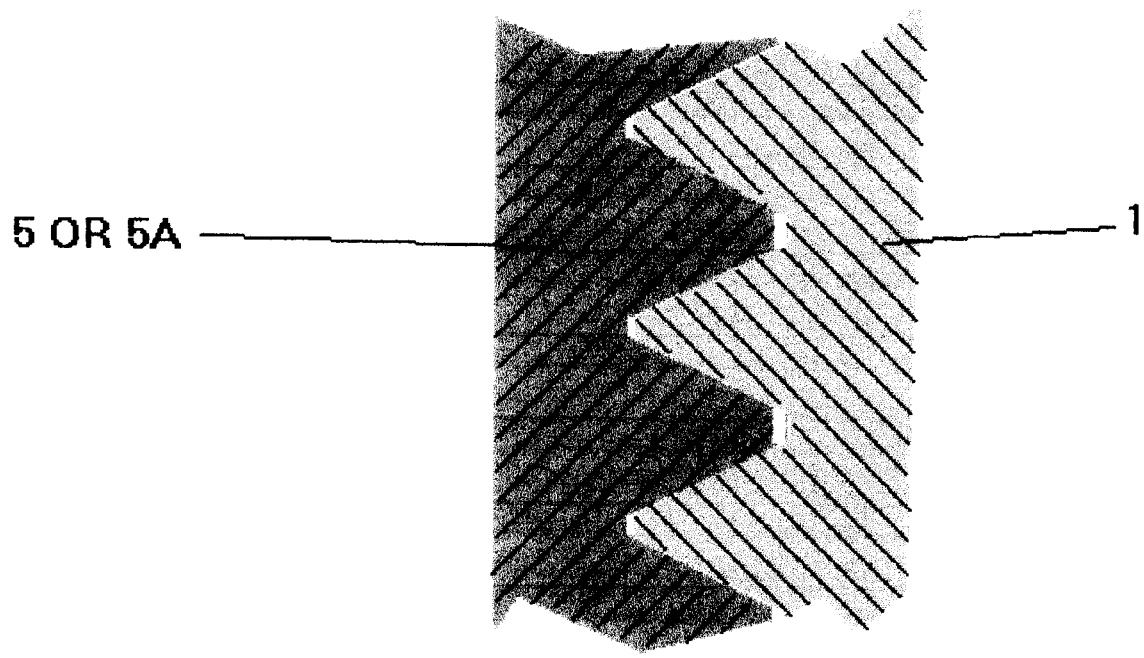
FIG. 3 is a vertical cross section perspective view of the mated thread configuration of the polishing stone and the threaded bolt.

FIG. 3 is a schematic view of the mated threads of the bolt 8a and the polishing stone 13. When mated there will be clearance present through out tolerances of the bolt threads 8a: major 16a and minor 16 diameters.

Figure 4:
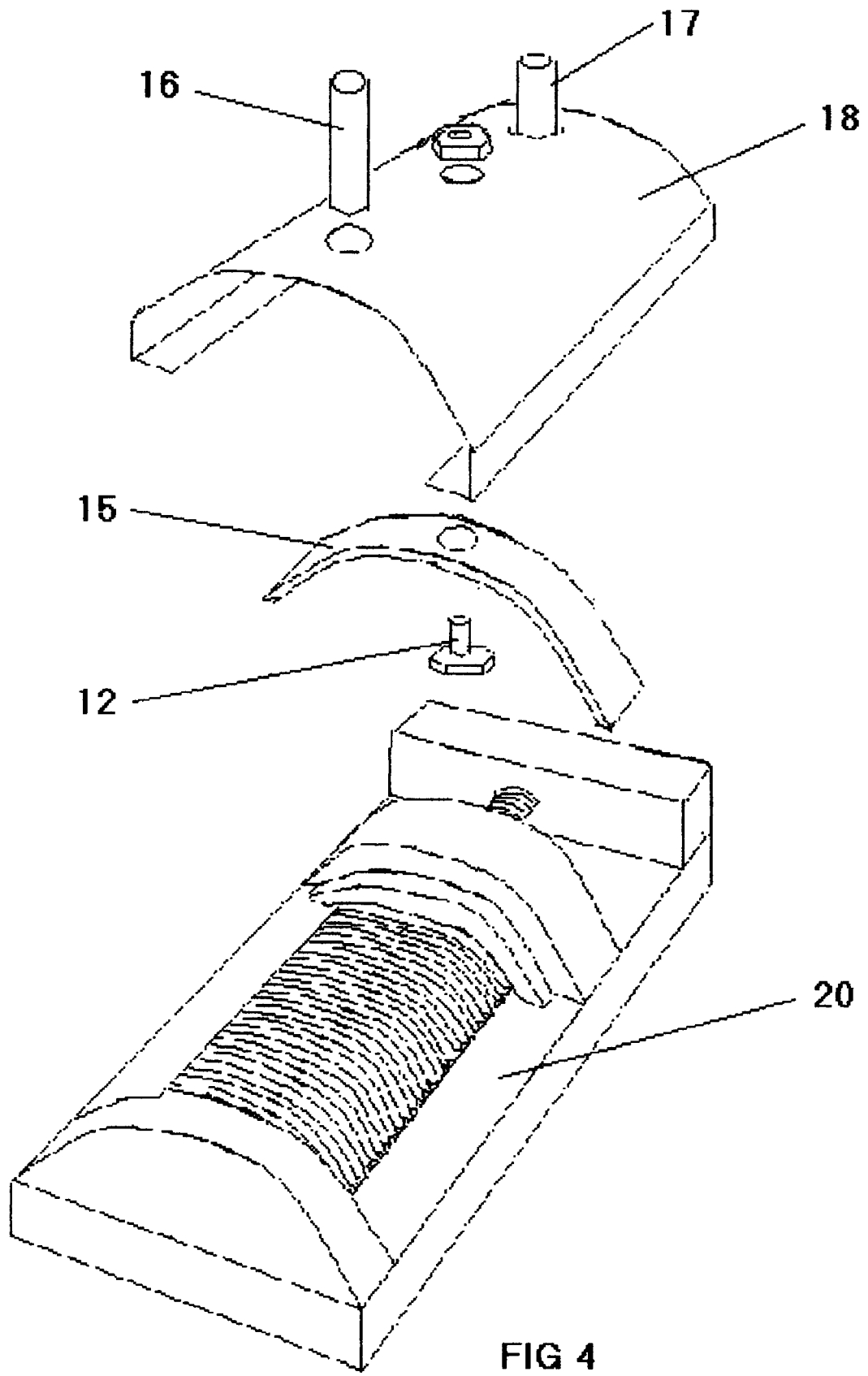
FIG. 4 is a perspective view of the polishing stone mold, fastening bolt, bolt securing bar, and mold cover.

FIG. 4 gives a perspective of the preferred molding process of the polishing stone. The stand pipes 17,19 are set into the sheet metal cover 20 while the holding nut 18 is mated to the connecting bolt 7 after it has been set through the bent bracing strap 21 and the sheet metal cover 20. This assembly is then placed over the mold 22 and the epoxy abrasive mixture is added.

Figure 5:
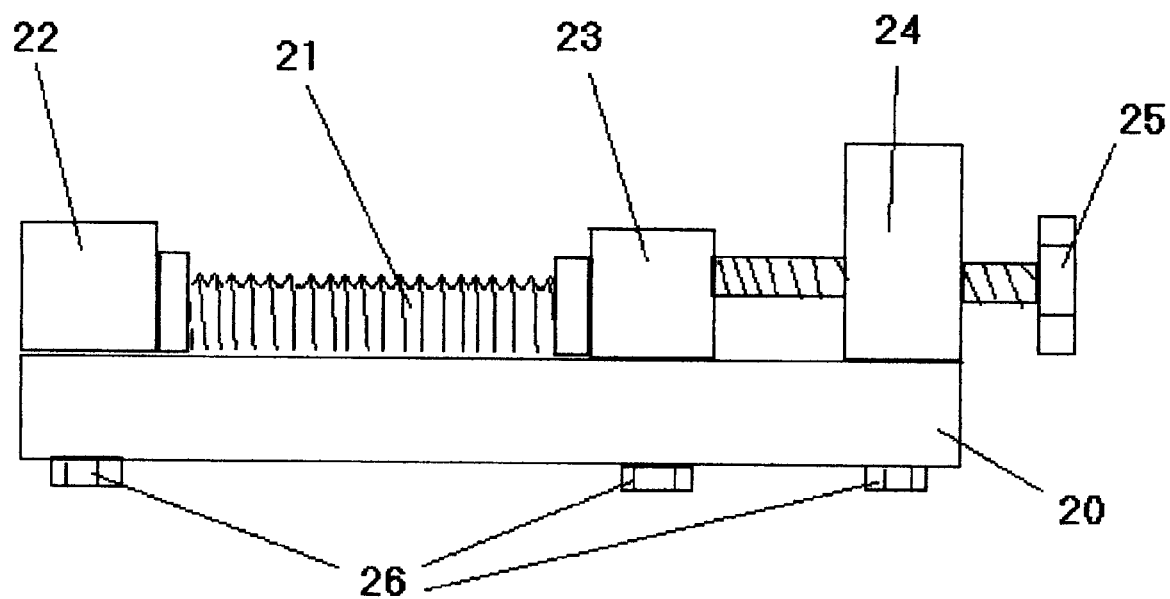
FIG. 5A is a side perspective of the mold, 5B is a side perspective of the mold threads.

FIG. 5 is the preferred embodiment of the mold. The thread piece 22c is made with external thread configuration using internal thread parameters, The length 23 is to be equal to the thread diameter, but not less than three inches. The end pieces 22a,22b, the thread piece 22c, and the jacking block 22d are secured to the base 22f by the retaining screws 22g. The jack screw 22e is tightened prior to attachment of the mold cover and the pouring of the epoxy abrasive mixture.

Although the preferred embodiment of the present invention has been described in the forgoing detailed description and illustrated in the forgoing drawings, it will be understood that the invention is not limited to the embodiment disclosed; but is capable of numerous modification, rearrangements, and substitution of parts without departing from the spirit of the invention.

Accordingly, the present invention is intended to encompass such modification, rearrangements, and substitutions of parts as fall within the scope and spirit of the appended claims.

I claim:

1. A device for inspecting and polishing threads on a bolt comprising:

a U-shaped frame having at least one pair of legs connected at their base, said base being located at a proximal end of the device;

polishing stones attached to the distal end of the frame;

a shank mounted proximate the proximal end of the device that cooperates with an external means for rotating the device.

2. The device of claim 1 wherein said polishing stones are molded from a mixture of epoxy-resin and abrasive powder.

3. The device of claim 2 wherein said polishing stones are formed in a mold that has external threads for molding internal threads of desired parameters in the polishing stones.

4. The device of claim 1 further comprising a spring-loaded clamp that cooperates with said legs for accommodating different sized bolts.

5. The device of claim 1 wherein said polishing stones are replaceable with other polishing stones of varying size, pitch and abrasiveness.

\* \* \* \* \*